United States Patent [19]

Heyden

[11] Patent Number: 4,637,389
[45] Date of Patent: Jan. 20, 1987

[54] TUBULAR DEVICE FOR INTUBATION

[76] Inventor: Eugene L. Heyden, S. 627 Bernard #8, Spokane, Wash. 99204

[21] Appl. No.: 721,168

[22] Filed: Apr. 8, 1985

[51] Int. Cl.$^4$ .......................................... A61M 16/00
[52] U.S. Cl. .................... 128/207.15; 604/35; 604/43
[58] Field of Search ............... 128/200.26, 207.15, 128/207.14, 207.16, 207.17, 911; 604/27, 35, 36, 604/40, 41, 43, 45, 173

[56] References Cited

U.S. PATENT DOCUMENTS

| | | | |
|---|---|---|---|
| 1,188,180 | 6/1916 | Kells . | |
| 2,491,647 | 12/1949 | Colavita | 128/275 |
| 2,614,563 | 10/1952 | Devine, Jr. | 128/276 |
| 3,173,418 | 3/1965 | Baran | 128/351 |
| 3,322,126 | 5/1967 | Rusch et al. | 128/351 |
| 3,384,089 | 5/1968 | Shriner | 128/350 |
| 3,421,510 | 1/1969 | Kettenbach | 128/350 |
| 3,426,759 | 2/1969 | Smith | 128/350 |
| 3,683,908 | 8/1972 | Michael et al. | 128/145.7 |
| 3,771,527 | 11/1973 | Ruisi | 128/350 |
| 3,788,326 | 1/1974 | Jacobs | 128/207.15 |
| 3,902,492 | 9/1975 | Greenhalgh | 128/241 |
| 4,037,605 | 7/1977 | Firth | 128/207.15 |
| 4,068,658 | 1/1978 | Berman | 128/200.26 |
| 4,090,518 | 5/1978 | Elam | 128/349 |
| 4,119,101 | 10/1978 | Igich | 128/351 |
| 4,156,428 | 5/1979 | Henkin | 128/207.15 |
| 4,166,468 | 9/1979 | Haynie | 128/351 |
| 4,168,699 | 9/1979 | Hauser | 128/768 |
| 4,275,724 | 6/1981 | Behrstock | 128/207 |
| 4,305,392 | 12/1981 | Chester | 128/276 |
| 4,316,459 | 8/1979 | Walski | 128/207.17 |
| 4,320,754 | 3/1982 | Watson et al. | 128/911 |
| 4,327,720 | 5/1982 | Bronson | 128/207.15 |
| 4,327,721 | 5/1982 | Goldin et al. | 128/207.15 |
| 4,351,328 | 9/1982 | Bodai | 128/207.15 |
| 4,405,308 | 9/1983 | Jessup | 604/200 |
| 4,435,174 | 3/1984 | Redmond et al. | 604/174 |
| 4,446,864 | 5/1984 | Watson | 128/207.14 |
| 4,449,563 | 5/1984 | Szachowicz et al. | 128/200.26 |
| 4,453,545 | 6/1984 | Inoue | 128/207.15 |
| 4,488,548 | 12/1984 | Agdanowski | 128/204.25 |
| 4,527,559 | 7/1985 | Roxbury et al. | 128/207.17 |

OTHER PUBLICATIONS

Arhelger, Tancheotomy and New Tracheal Tube, Surgery, Feb. 1951, pp. 260-266.
Advertising sheet for NCC Division Mallinckrodt, Inc.'s, "Hi-Lo Jet Tracheal Tube", NCC Division Mallinckrodt, Inc., Hook Road, Argyle, NY 12809.

Primary Examiner—Henry J. Recla

[57] ABSTRACT

A tracheal tube (20) provides an expansible channel (40) along its length. The channel normally maintains a generally concealed attitude within the trachael tube wall and adapts by expansion for the insertion of a suction catheter (60), guiding the catheter at various depths within the channel for the removal of secretions and other substances which accumulate around the tube when in use within the intubated pathway. Ports (46), located at strategic locations along the tube wall and leading to the channel, afford access to these accumulations. Among the various embodiments of the invention is a valve-like arrangement which opens the ports only when a catheter is inserted within the channel. Also, a novel means for directing and concentrating suction forces at individual ports is disclosed.

30 Claims, 9 Drawing Figures

TUBULAR DEVICE FOR INTUBATION

This application is a continuationin-part of an earlier application filed on Sept. 24, 1984, Ser. No. 655, 089 entitled APPARATUS FOR INTUBATION.

BACKGROUND OF THE INVENTION

This invention relates generally to tubular medical devices intended for insertion and extended stay within a body pathway. Relating more particularly to tracheal tubes such as endotracheal and tracheostomy tubes, the present invention is directed to the effective removal of secretions and the like which accumulate between the tracheal tube and the wall of the intubated pathway.

Conventionally, the tracheal tube comprises an elongated tubular device of resilient material, arcuate in its longitudinal extent, providing a wall which defines a continuous central fluid passage. When intubated within the breathing pathway, a forward segment and end resides in the trachea and a rearward segment and end resides outside the remainder of the breathing pathway, extending through the mouth, naris, or tracheostomy of a patient. A circumferentially expansible cuff is a predominate tracheal tube feature and resides near its forward end. Inflated to provide a seal with the tracheal wall, the cuff acts to prevent the escape of respiratory gasses exchanged between the tracheal tube and the lungs and, at the same time, functions to prevent a variety of substances which accumulate within and along the intubated pathway from entering the lower respiratory system.

As mentioned, secretions and other substances commonly accumulate between the tracheal tube and the inner wall of the intubated pathway and range from upper airway secretions, lower airway secretions "blown" upward past the cuff during paroxysms of coughing or ventilation modes such as PEEP and HFJV, hemorrhagic fluids, refluxed or vomited gastric contents, to surgical debris. Accidental aspiration is not uncommon and occurs during the extubation proceedure and during periods of accidental cuff deflation or inappropriately low cuff inflation states. Pneumonia and other pathological conditions can result, leading to serious sequelae and prolonged and complicated hospitalization.

Effective removal of secretions and other accumulations is a clinical necessity, not only to prevent medical complications but also to meet the hygienic care and comfort needs of the patient. Attempts to remove these accumulations on the part of the patient by swallowing efforts contributes to the discomfort and irritation associated with intubation by causing muscular contractions around the tube and sliding movement between the tube and the wall of the intubated pathway. Consequently, injury can occur in areas of tube-tissue contact, particularly in the interarytenoid region, by such tube-tissue interaction. Inserting a suction catheter beside and along the tracheal tube wall is an additional source of discomfort and irritation as cough and gag reflexes are stimulated. Forceful contact between the catheter and tissue structure also occurs and suction entrapment of tissue by applied suction forces is unavoidable all of which is counterproductive, noxious, and traumatizing in effect. Furthermore, control of the suction catheter is difficult, making insertion of the catheter to the vicinity of the forward segment and cuff difficult to achieve. Often, as in the case of the orally or nasally intubated patent, the suction catheter is unintentionally inserted into the esophogus rather than following the more difficult path into the trachea.

SUMMARY OF THE INVENTION

The present invention, as illustrated in preferred embodiments, provides a tracheal tube that allows for the effective removal of secretions which accumulate outside the length of the tube above the expansible cuff. Specifically, a channel of long longitudinal extent is defined within the tracheal tube wall and is adapted to guide movement of a suction catheter within and along a substantial length of the tube. Drainage ports provide fluid communication between the outside of the tracheal tube and the region within the channel and are directed bilaterally away from midline to eliminate blockage thereof by resting contact with the surface of the intubated passage. Furthermore, the channel can be so defined within the tube as to require no additional bulk or material requirements for its provision, taking on a somewhat concealed attitude within the tracheal tube wall the channel and is adapted to enlarge in width as a wall portion providing the channel deforms from its normal position within the tracheal tube wall in accommodation of an inserted catheter. The position of the channel, along the outside curvature of the tube, provides access to locations most favorable to accumulation build up in the recumbent patient. By protecting the suction catheter (or other implement such as a temperature probe or an irrigation or medicating catheter) from direct contact with the tissue and structures of the intubated pathway, subsequent trauma or noxious stimulation during catheter usage is avoided. One embodiment provides a channel and port arrangement particularly suitable for use in tracheal tubes of the uncuffed variety. And, in use with a specially mated suction catheter, suction forces can be directed and concentrated within the channel toward individual ports in alternating sequence.

BRIEF DESCRIPTION OF THE ACCOMPANYING DRAWINGS

The invention can best be understood in conjunction with the accompanying drawings to which the description of preferred embodiments correspond.

FIG. 1 is a perspective view of a tracheal tube according to the preferred embodiment of the present invention, illustrated as correctly intubated within the trachea of a patient;

FIGS. 2 and 3 are enlarged cross-sections taken along line 2—2 and line 3—3 of FIG. 1, respectively;

FIG. 4 is a sectional view of a tracheal tube segment according to the present invention, particularly pointing out the relationship and action of the device in relation to an associated suction catheter;

FIGS. 5 and 6 are enlarged cross-sectional views of alternative embodiments of the present invention similar to the cross-section taken from line 2—2 in FIG. 1; and, FIG. 7 illustrates another embodiment of the present invention in cross-section, and can additionally be taken along with FIGS. 8 and 9 to teach yet another embodiment of the invention.

DETAILED DESCRIPTION OF THE INVENTION

Figure 1:
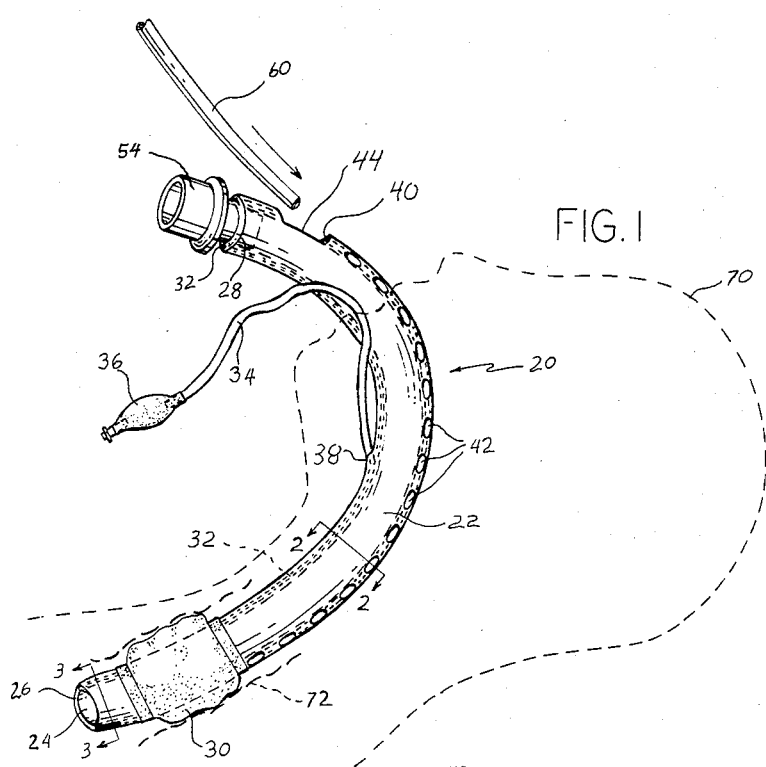
Figure 2:
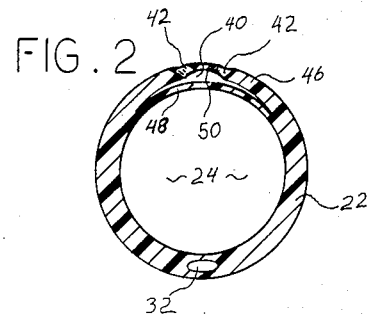
Figure 3:
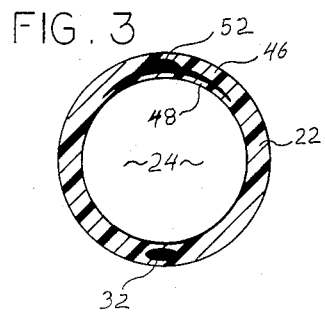

Referring particularly to FIGS. 1, 2, and 3, the tracheal tube 20 of the preferred embodiment is shown and comprises a longitudinally curved tubular member 22 providing a cross-sectionally continuous wall, having a forward end 26 and an opposing rearward end 28. The material used in its construction is of a resilient plastic material.

The tracheal tube 20 is adapted for partial insertion within the breathing pathway, having a major portion residing therein, with the forward end 26 within the trachea 72 and the rearward end 28 extending outside the patient 70 through a body opening. A central fluid passage 24, continuous in length with the tubular member 22, comprises the major cross-sectional area of the tracheal tube. As a fluid passage, the central fluid passage 24 provides for the exchange of respiratory gasses to and from the patient's lungs.

An additional feature, common to tracheal tubes, is the expansible cuff 30 carried upon the tubular member 22 in the vicinity of its forward end 26. Used to provide a seal with the tracheal wall, the cuff 30 acts to prevent the escape of respiratory gasses meant for delivery to the lungs and, at the same time, acts to prevent a variety of substances which tend to accumulate above the cuff and along the intubated pathway from entering the lower respiratory tract. An inflation circuit is employed to inflate (or deflate) the cuff and includes an inflation tube 34, a formed attachment 38 joining one end of the inflation tube 34 with an inflation lumen 32 which is integral with the wall of the tubular member 22, a check valve and pilot balloon assembly 36 carried at the other end of the inflation tube 34, and fluid communication means (not shown) between the inflation passage 32 and the inside of the cuff 30. The inflation passage 32 is occluded (shown by darkened area 32, FIG. 3) at the forward end 26 of the trachael tube, acting to sustain the cuff in an inflated condition. It is crucial that the cuff maintain an inflated state and sealing function during use to ensure proper ventilation and to protect the lower airway from insult.

In FIG. 1, the tracheal tube is shown as it would appear correctly and commonly intubated within a patient. The forward end 26 and cuff 30 are illustrated as being properly positioned within the trachea 72 of a representative patient 70. The tubular member 22 extends the rearward end 28 of the device outside the mouth of the patient and supports thereat a connector 54 for joining to a ventilation apparatus (not shown).

The tracheal tube is improved according to the present invention by the provision of means to manage substance accumulations which occur between the tube and the wall of the intubated pathway. Specifically, an elongated channel 40 is integrally formed within the wall of the tubular member 22 and extends functionally a substantial length between the forward end 26 and the rearward end 28, providing for insertion and depth adjustment of a suction implement or catheter 60 therewithin. The channel 40 is preferably placed along the outside curvature of the tube 20 to assume a position within the intubated pathway most favorable for access to secretions and other substances, being adjacent to the lowest regions of the intubated pathway where gravitational forces promote their accumulation in the recumbent patient. Ports 42 are spaced at locations along opposing sides of an outer wall portion (46) of the tubular member 22 and reside between the rearward end 28 and the expansible cuff 30, providing fluid communication between the region outside the tubular member 22 and the channel 40. The ports 42, being in opposing rows, are directed bilaterally away from a midline position along the tubular member 22 to prevent their occlusion in midline areas where resting contact with the surface of the intubated pathway occurs; and also, a wider area of influence to suction forces is achieved by the placement of ports bilaterally away from midline. An inward curvature 50 in the inner surface of said first wall portion 46, midline and between the rows of ports, aids in centering the catheter between opposing ports. An opening 44 in the vicinity of the rearward end 28 of the tube provides an entrance to within the channel 40. And, the channel 40 is effectively terminated (darkened area 52, FIGS. 1 and 3) in the vicinity of the forward end 26 to prevent communication and catheter extention beyond the forward end. A significant feature of the channel will be discussed presently, with particular reference to FIG. 4.

Figure 4:
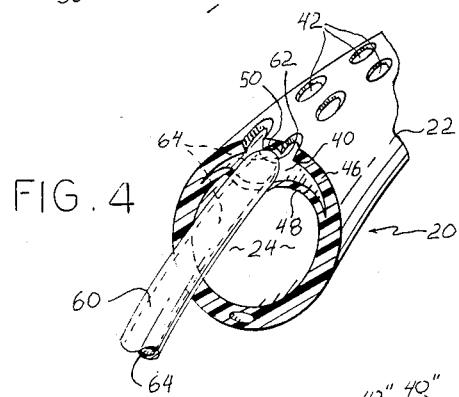

As noted above, the channel 40 provides for insertion and depth adjustment therein by a suction catheter 60. A charcteristic of particular advantage is the attitude which the channel assumes within the tubular member 22. Defined within the wall of the tubular member between an outermost first wall portion 46 and an innermost second wall portion 48, the channel normally assumes a somewhat concealed attitude therewithin. However, being responsive to the insertion of a catheter 60, as illustrated in FIG. 4 (a section of tracheal tube according to the preferred embodiment), the channel responsively expands in size, correspondingly increasing the space relation between the first and second wall portions, causing the second wall portion 48 to be urged toward and within the area normal to the central fluid passage 24. In an area of confining dimension, such a characteristic of the breathing pathway, this becomes an important feature. As a structural addition to the tracheal tube, the channel 40 requires for its provision no objectionable increase in the outside diameter of the trachael tube or requires a decrese in the size of the central fluid passage 24 or internal diameter of the tube, yet the channel is adaptable to be of sufficient size to accommodate the relatively large size of suction catheter needed for effective secretion removal. As a further consideration, it is advantageous that the first wall portion 46 be of an adequate thickness to maintain the shape and structural integrety of the tubular member 22 and that the inner second wall portion 48 be of a lesser thickness so as to be more resilient or yieldable during the accommodation and directional urging of the catheter 60. It is also a consideration of the present invention that a degree strength be maintained by the second wall portion 48 sufficient to support the suction catheter 60 in its position in the inward curvature 50 of the first wall portion 46 and to return the channel 40 again to its concealed attitude when the catheter is removed.

In light of the foregoing, it can readily be appreciated that, as an operator guides a suction catheter 60 in and along the channel 40, substances which passively flow through the ports and into the channel are promptly removed by suction and the ports nearest to the tip 62 and forward origin of the catheter lumen 64 are active in the transport of substances from within the intubated pathway, into the channel 40, and subsequently out both through the suction catheter. It can also be appreciated that the extent of encroachment on the area normal to the central fluid passage by a deformed second wall portion 48 is minimal and could be brief and periodic in nature as to not appreciably interfere with the ventilating function of the tracheal tube. Additionally, it can be appreciated that the channel 40 would be useful for the insertion of implements other than suction catheters, such as a temperature probe, a medicating or irrigating catheter, or an intubation stylet.

As previously mentioned, the channel 40 is terminated in the vicinity of the forward end 26. In the preferred embodiment a radiopaque filling 52 is used to accomplish this purpose and, at the same time, is useful to provide for radiographic determination of the forward end of the tracheal tube.

Figure 5:
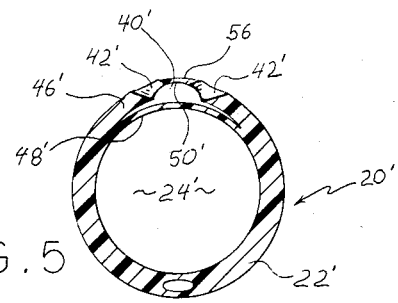

FIG. 5 is a cross-sectional view teaching an alternative embodiment of the present invention. As in the preferred embodiment, the tracheal tube 20' includes a tubular member 22', a central fluid passage 24", and a channel 40' defined by an outermost first wall portion 46' and an innermost second wall portion 48', all substantially positioned as in the preferred embodiment. Ports 46' leading to the channel 40' are also directed away from midline. In this embodiment, however, an outward protrusion 56 of the first wall portion, along with its inward curvature 50', exists and provides a wall area in the tubular member 22' larger in thickness than the normal thickness of the remainder of the tubular member. Thus, a larger catheter can be accommodated within the channel 40' without a corresponding increase in the extent which the second wall portion 48' would be urged within the area normal to the central fluid passage 24'; additionally, the channel 40' is projected in an outward direction to achieve a closer approximation with the wall of the intubated pathway. The ports 42' may also be extended in a more lateral direction to decrease the occurrence of occlusive contact with the surface of the intubated pathway.

Figure 6:
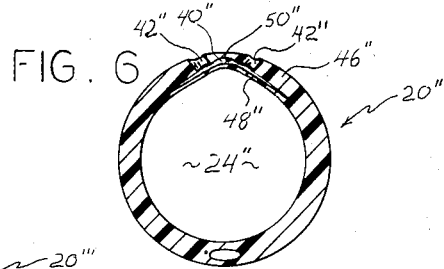

FIG. 6 is a cross-sectional view of an additional embodiment of the invention. As in the preferred embodiment, the tracheal tube 20" includes a tubular member 22", a central fluid passage 24", and a channel 40" defined between a first wall portion 46" and a second wall portion 48", likewise substantially positioned as in the preferred embodiment. In this embodiment, however, the second wall portion 48" normally holds a position against the first wall portion 46" in an attitude that substantially blocks the ports 42" to fluid communication. It can be appreciated that when a catheter is inserted within the channel 40", a corresponding separation between the first and second wall portions opens the ports 42" for fluid communication; and removal of the catheter returns the resilient second wall portion 48" again in an attitude blocking the ports. This feature would be particularly useful in uncuffed tracheal tubes to prevent substances from migrating from a higher port, into and along the channel, and out through a lower port with possible entrance within the lower respiratory system. A cuff would normally block this migration to the lower respiratory system, but in situations where a cuff is not used, or this feature would be otherwise desired, this valve-like arrangement would be highly advantgeous.

Figure 7:
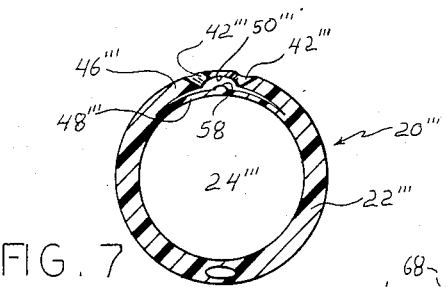

FIG. 7 is yet another embodiment of the present invention presented in cross-section. In addition to a central fluid passage 24''' defined by tubular member 22''' and a catheter guiding channel 40''' defined by a first wall portion 46''' and a second wall portion 48''', a small ridge 58 is shown extending from the second wall portion 48''' toward the inward curvature 50''' of the first wall portion 46'''. Extending the length of the channel 40''', the ridge 58 acts as a bearing surface to reduce the extent of contact and friction between the catheter and second wall portion 48''', easing movement of the catheter within the channel.

Figure 8:
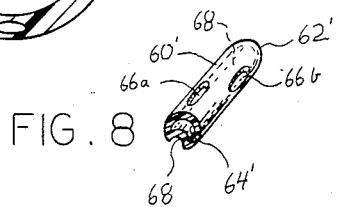
Figure 9:
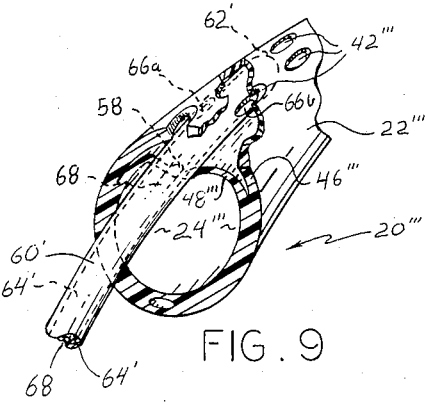

Again referring to FIG. 7, and taken together with FIG. 8, an additional embodiment of the invention can be understood and is shown accordingly in a corresponding sectional view, FIG. 9. In addition to the bearing surface characteristic of the ridge 58, this structure can also be useful to mate with a longitudinally extending groove 68 within the outer wall of a catheter 60', substantially as illustrated in FIG. 8, and would coact therewith to align portions of the catheter within the channel 40'''' and to prevent catheter rotation and misalignment. A catheter configuration 60', such as shown sectionally in FIGS. 8 and 9, including two forwardly disposed and laterally directed suction apertures 66a and 66b in communication with the central catheter lumen 64", and disposed on the side of the catheter opposing the longitudinal groove 68, is used to direct the suction forces toward the locations of opposing ports 42'''. The lumen 64" of the catheter 60" does not communicate beyond the catheter tip 62" as does the catheter shown in FIG. 4. A stronger pull by the suction force can therefore be exerted by this exemplary method of directing, which illustrates the advantage of using a catheter configuration mated together with a channel configuration in such a manner as to achieve and maintain purposeful alignment. Furthermore, if the apertures 66a and 66b lag in placement, one behind the other, along opposing sides of the catheter 60', as shown in FIGS. 8 and 9, suction forces can be directed toward the ports 42''', one port at a time, producing a further concentrating of suction forces toward accumulations. That is, when one aperature (66b) is in register and acting with one port, the other aperature (66a) is out-of-register with opposing ports and closed to suction by its close approximation to the first wall portion 46'''.

As can be readily understood from the foregoing, the practice of the invention may be according to various embodiments and is not to be interpreted in scope exclusively thereto, but according to the appended claims.

In keeping with both the foregoing description of the invention and the intent thereof, what is claimed is:

1. A tubular device for intubation of a body pathway, comprising:

an elongated tubular member of resilient material providing a wall with an inner wall surface and an outer wall surface, having a forward segment and end for residing within a body pathway, and also having a rearward segment and end for residing outside a body pathway, said tubular member defining a central axis and a central fluid passage extending therethrough;

an elongated guide means provided by said tubular member adapted and longitudinally sufficient for slidably receiving a suction catheter and guiding the same along a substantial length of said tubular member directionally away from the vicinity of said rearward end toward said forward end, said guide means defined within the wall of said tubular member between said inner wall and said outer wall surfaces for defining a region therein for the accommodation of said suction catheter, said guide means further adapted to modify in configuration from a normally unexpanded attitude to an expanded attitude when accommodating said suction catheter; and fluid communication means for providing fluid communication between the region within said guide means and said body pathway, said fluid communication means provided by the wall of said tubular member and residing in locations adjacent said guide means between said forward and said rearward ends, said fluid communication means also residing in a plurality of locations along the wall of said tubular member adjacent a plurality of locations within said guide means for providing fluid communication over a substantial length of said guide means between said region and said body pathway, whereby said suction catheter can remove secretions over any of several locations along said tubular member when moved at various depths within said guide means.

2. The device of claim 1, wherein said guide means includes a channel defined within the wall of said tubular member between a first wall portion and a second wall portion, said first wall portion outermost in its position with respect to said second wall portion and having said fluid communication means defined therein, said second wall portion innermost in its position with respect to said first wall portion and adapted to achieve a position directionally away from said first wall portion when accommodating said suction catheter.

3. The device of claim 2, wherein said channel is defined between the inner and outer wall surfaces of said tubular member and also defined between said first and said second wall portions; and said fluid communication means comprises a plurality of spaced-apart ports, said ports disposed in said first wall portion leading from the outer wall surface of said tubular member to within said channel.

4. The device of claim 3, wherein said first wall portion includes opposing sides and a midline, said ports located on said opposing sides and also directed away from said midline.

5. The device of claim 4 wherein said channel includes means for aligning said suction catheter in a midline location within said channel and with respect to the opposing sides of said first wall portion.

6. The device of claim 5, wherein said alignment means includes a curved region longitudinally defined by said first wall portion on an inner surface thereof facing said second wall portion, said curved region having a midportion of longitudinal extent most distant from said second wall portion.

7. The device of claim 3, wherein said first wall portion has a midline location of longitudinal extent which protrudes radially outward from the central axis of said tubular member, and said ports are located laterally away from said midline location.

8. The device of claim 2, wherein said tubular member maintains a normal and substantially uniform spacing between said inner wall and said outer wall surfaces throughout its cross-sectional extent, said uniform spacing including an area of said tubular member providing said channel.

9. The device of claim 2, wherein said second wall portion is actuated directionally away from said first wall portion when said suction catheter is accommodated within said channel.

10. The device of claim 2, wherein said first and said second wall portions are of a given thickness and corresponding resiliency, said second wall portion being thinner and more resilient than said first wall portion.

11. The device of claim 2, wherein said tubular member includes an expansible cuff in joined relation thereto, said cuff carried upon the forward segment of said tubular member in the vicinity of said forward end, said channel extending forward at least to the vicinity of said cuff, and said fluid communication means resides in locations between the rearward end of said tubular member and said cuff.

12. The device of claim 2, wherein said channel is included in the rearward segment of said tubular member in the vicinity of said rearward end, and access means is provided by said tubular member in the rearward segment thereof for the insertion of said suction catheter therethrough for entry to within said channel.

13. The device of claim 12, wherein said access means includes an opening in said first wall portion leading to said channel.

14. The device of claim 2, wherein said second wall portion is defined between said first wall portion and said central axis; and said second wall portion is reversably extendable toward said central axis while accommodating said suction catheter.

15. The device of claim 14, wherein said first and said second wall portions are normally in a substantially approximated attitude;

said communication means comprises a plurality of spaced-apart ports, said ports disposed in said first wall portion leading from the outer wall surface of said tubular member to within said channel; and said second wall portion acts to block said ports when maintained in an approximated attitude with said first wall portion, said first and said second wall portions being separable for accommodating said suction catheter and separable for unblocking said ports.

16. The device of claim 2, wherein said channel is included in the forward segment of said tubular member in the vicinity of said forward end, and said channel has occlusion means associated therewith for preventing communication between the region defined by said channel and a region beyond the forward end of said tubular member, said occlusion means provided to prevent the extension of said suction catheter beyond said forward end.

17. The device of claim 16, wherein said occlusion means includes a radiopaque material occlusively deposited within said channel.

18. The device of claim 2, wherein said tubular member is arcuate in a relaxed state, said tubular member having a convex side and an opposing concave side, said channel located on the convex side of said tubular member.

19. The device of claim 2, wherein said channel includes friction reducing means for reducing friction between said suction catheter and a surface of said channel as said suction catheter is moved therein, said friction reducing means comprising a longitudinally extending ridge depending from a wall portion defining said channel and projecting within the region defined by said channel.

20. The device of claim 2, wherein a longitudinally extending ridge exists integral with a wall portion providing said channel and projects within the region defined by the same, said ridge defining means suitable for mating with a longitudinally extending groove provided by a suction catheter for aiding in preventing the rotation of said suction catheter within said channel.

21. An arrangement for removing substances from within a body pathway by suction, comprising:

an elongated tubular member providing a wall with an inner wall surface and an outer wall surface, having a forward segment and end for residing within a body pathway, and also having a rearward segment and end for residing outside a body pathway, said tubular member defining a central axis and a central fluid passage extending within from said forward end to said rearward end;

an elongated guide means provided by said tubular member adapted and longitudinally sufficient for slidably receiving a suction catheter and guiding the same along a substantial length of said tubular member directionally away from the vicinity of said rearward end and a substantial distance toward said forward end, said guide means defined within the wall of said tubular member between said inner wall and said outer wall surfaces for defining a region therein for the accommodation of said suction catheter;

fluid communication means located to provide fluid communication between said guide means and said body pathway, said fluid communication means provided by the wall of said tubular member and residing in locations adjacent said guide means between the forward and rearward ends of said tubular member, and said fluid communication means also residing in a plurality of locations along the wall of said tubular member adjacent a plurality of locations within said guide means for providing fluid communication over a substantial length of said guide means between said region and said body pathway;

an elongated suction catheter including a catheter wall defining a central lumen, a forward termination, and apertured means communicating with said central lumen and residing in the vicinity of said forward termination, said fluid communication means; and alignment means for aligning said aperatured means within said guide means for a registry with said fluid communication means;

whereby said suction catheter can remove secretions over any of several locations along said tubular member when moved at various depths within said guide means, and whereby said aperatured means achieves a registry with said fluid communication means as said suction catheter is guided to various positions within said guide means.

22. The arrangement of claim 21, wherein said guide means includes a channel integrally formed within the wall of said tubular member, and said fluid communication means is formed within said wall leading from the outer wall surface of said tubular member to the region defined by said channel; and said alignment means comprises a coacting relation between said channel and said suction catheter to align said aperatured means directionally toward said fluid communication means, said coacting relation provided for preventing the rotation of said suction catheter and a subsequent misalignment between said fluid communication means and said aperatured means.

23. The arrangement of claim 22, wherein said fluid communication means comprises a plurality of ports at spaced-apart locations formed within and along the wall of said tubular member; and said channel is formed within the wall of said tubular member between said inner and said outer wall surfaces and between said outer wall surface and said central fluid passage, said channel also defined between a first wall portion and a second wall portion, said first wall portion outermost in its position with respect to said second wall portion and providing said ports therein, said second wall portion innermost in its position with respect to said first wall portion and adjacent said central fluid passage.

24. The arrangement of claim 23, wherein said channel is expansible, and said inner wall portion is actuated away from said first wall portion and toward said central axis when accommodating said suction catheter.

25. The arrangement of claim 23, wherein said channel is configured to include an inwardly extending longitudinal projection projecting within the region defined by said channel, said projection integral to an inner surface of said tubular member, and said suction catheter is configured to include a longitudinally extending groove for mating with said projection, whereby orientation of said aperatured means is maintained directionally toward said ports by said mated relation while said suction catheter is accommodated within said channel.

26. The arrangement of claim 23, wherein the wall of said tubular member includes opposing sides and a midline, and said ports are located in rows along opposing sides of said midline;

said suction catheter also includes opposing sides and a midline, said aperatured means included in opposing sides; and said aperatured means is arranged to achieve selective registry and close approximation with said ports as they reside situated in opposing rows.

27. The arrangement of claim 26, wherein said ports are arranged in spaced-relation with each other, and said aperatured means achieves a registry with one of said ports and, at the same time, achieves a substantially out-of-registry relation with the remainder of said ports.

28. The arrangement of claim 27, wherein said ports are positioned substantially parallel one port with another corresponding port residing in the opposing row; and said aperatured means includes at least two opposing aperatures, a first aperature directed for registry with one row of ports, a second aperature directed for registry with the opposing row of ports, said first and second aperatures arranged in spaced-relation with each other, one of said aperatures a substantial distance closer to the forward termination of said suction catheter than another of said aperatures whereby one aperature can achieve registry with one port while the other aperature is substantially out of registry with a corresponding and opposing port residing in the opposing row;

whereby suction forces can be directed through said aperatures one port at a time, and said ports can be suctioned one port at a time as said suction catheter is moved to various positions within said channel.

29. The arrangement of claim 23, wherein said tubular member includes an expansible cuff, said expansible cuff carried upon the forward segment of said tubular member in the vicinity of said forward end, wherein said channel extends at least to the vicinity of said cuff, and said ports reside in locations between the rearward end of said tubular member and said cuff.

30. The arrangement of claim 22, wherein said coacting relation includes a configuration of said suction catheter adapted to mate with a configuration of said channel.

* * * * *

UNITED STATES PATENT AND TRADEMARK OFFICE
CERTIFICATE OF CORRECTION

PATENT NO. : 4,637,389
DATED : Jan. 20, 1987
INVENTOR(S) : Eugene L. Heyden

It is certified that error appears in the above-identified patent and that said Letters Patent are hereby corrected as shown below:

Col. 1, line 4, "continuationin-part" should be --continuation-in-part--.
Col. 1, line 6, after "INTUBATION" insert --, now U.S. Patent No. 4,607,635--.
Col. 1, line 63, place a comma after "unavoidable".
Col. 2, line 10, delete "long".

Col. 4, line 32, "a" should be --as--.
Col. 5, line 13, "24'' " should be --24'--.
Col. 5, line 63, "46'' " should be --46'''--.
Col. 9, line 36, after "termination," insert --said apertured means located for registery with--.
Col. 10, line 38, insert a comma after "parallel".
Col. 6, 9 and 10, "aperature" is a misspelling and should be --aperture-- in each occurrence.

Signed and Sealed this

Thirteenth Day of October, 1987

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,637,389

DATED : Jan. 20, 1987

INVENTOR(S) : Eugene L. Heyden

It is certified that error appears in the above-identified patent and that said Letters Patent is hereby corrected as shown below:

Column 2, line 22, place a period after "wall" and capitalize "the".

Signed and Sealed this

Eighth Day of March, 1988

Attest:

DONALD J. QUIGG

*Attesting Officer*      *Commissioner of Patents and Trademarks*